(12) United States Patent
Ghabra (10) Patent No.: US 8,968,399 B2
(45) Date of Patent: Mar. 3, 2015

(54) INTRAOCULAR LENS

(76) Inventor: Marwan Ghabra, Damascus (SY)

(*) Notice: Subject to any disclaimer, the term of this patent is extended or adjusted under 35 U.S.C. 154(b) by 440 days.

(21) Appl. No.: 13/518,500

(22) PCT Filed: Dec. 21, 2010

(86) PCT No.: PCT/GB2010/002303
§ 371 (c)(1),
(2), (4) Date: Jan. 15, 2013

(87) PCT Pub. No.: WO2011/077079
PCT Pub. Date: Jun. 30, 2011

(65) Prior Publication Data
US 2013/0110233 A1 May 2, 2013

(30) Foreign Application Priority Data
Dec. 22, 2009 (GB) .................................. 0922461.9

(51) Int. Cl.
*A61F 2/16* (2006.01)
*G02C 7/08* (2006.01)

(52) U.S. Cl.
CPC .............. *A61F 2/1662* (2013.01); *A61F 2/1624* (2013.01); *A61F 2/1648* (2013.01); *G02C 7/081* (2013.01); *A61F 2/1629* (2013.01); *A61F 2/1632* (2013.01)

USPC .......................... 623/6.34; 623/6.37; 623/6.32

(58) Field of Classification Search
USPC .......................... 623/6.32–6.34, 4.1
See application file for complete search history.

(56) References Cited

U.S. PATENT DOCUMENTS 4,198,980 A * 4/1980 Clark ............................ 606/107
6,921,416 B2 * 7/2005 Khoury ........................ 623/6.37

* cited by examiner

*Primary Examiner* — David H Willse
*Assistant Examiner* — Tiffany Shipmon
(74) *Attorney, Agent, or Firm* — Fogg & Powers LLC (57) ABSTRACT

A vision correction arrangement is described in which a lens system having variable optical power varies in dependence on the orientation of the user's eye. The vision correction arrangement may be embodied as an intraocular lens implant, or an extraocular device such as spectacles. The intraocular lens implant comprises a fixed lens element (11) and a movable lens (12) element sensitive to the orientation of the eye, so that the optical power of the intraocular lens implant is increased when the user looks downward, and returns to a reduced optical power condition when the user's eye returns to a horizontal gaze. The fixed lens element may have a convex rear surface and a concave front surface, and the second lens element may be pivotally mounted in front of the first lens element, so that downward inclination of the eye causes the second lens element to swing away from the fixed lens element.

16 Claims, 5 Drawing Sheets

INTRAOCULAR LENS

This application claims priority to International Patent Application No. PCT/GB2010/002303 filed on Dec. 21, 2010, which claims priority to GB Patent Application No. 0922461.9 filed on Dec. 22, 2009.

The present invention relates to the correction of eyesight defects, and is particularly concerned with a lens arrangement having two-part optics in which first and second optical elements are relatively movable to vary the optical power of the lens arrangement, in dependence on the direction of the user's gaze relative to the horizontal.

Figure 1:
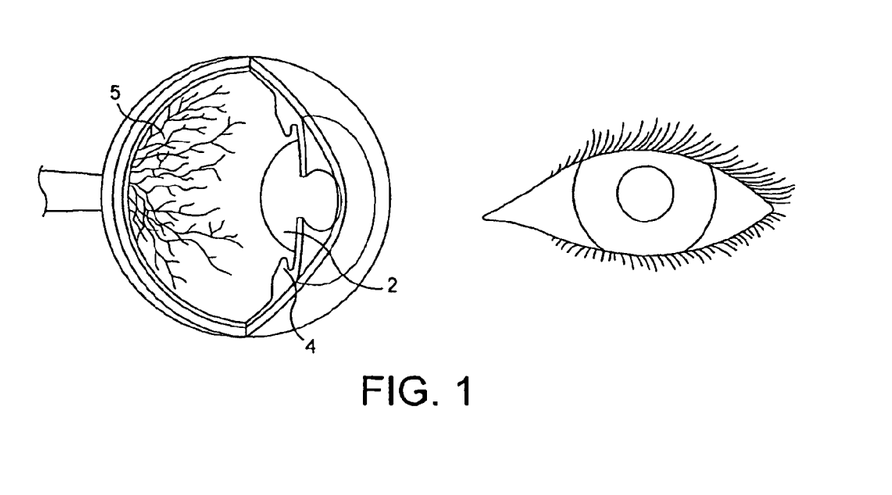
FIG. 1 and FIG. 2 illustrate the structure of the human eye, FIG. 1 providing a cutaway perspective view and FIG. 2 a central vertical sectional view.
Figure 2:
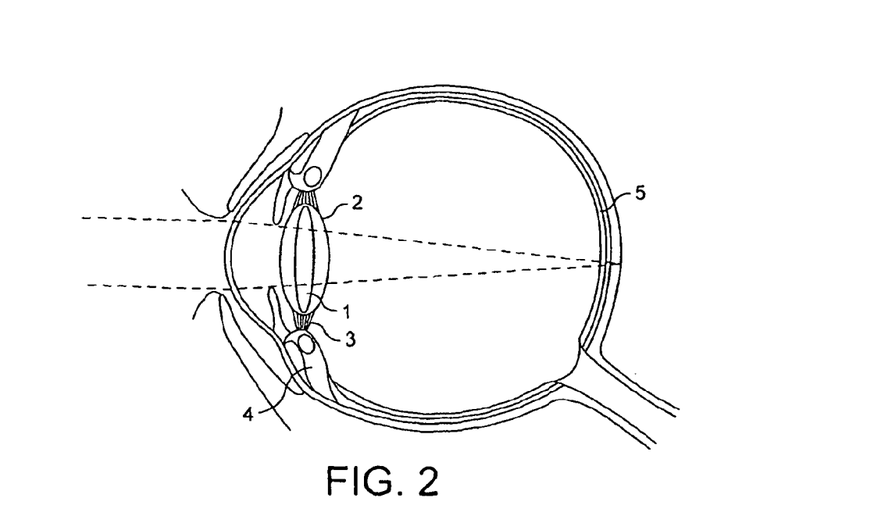

In the human eye, as is illustrated in FIGS. 1 and 2, the lens 1 is contained within a capsule 2, and the capsule 2 is suspended by ligaments 3 from the ciliary body 4. The lens 1 and the capsule 2 are formed of elastic tissue. The ciliary body 4 is a ring-like muscle which extends around the capsule and which, when contracted, reduces the diameter of the capsule 2 and the lens 1, thus thickening the lens and increasing its optical power so that objects a short distance from the eye are brought into sharp focus on the retina 5. When the ciliary body 4 is relaxed, the elasticity of the capsule 2 and the lens 1 returns them to their original diameter, with the lens 1 now thinner and able to focus distant objects clearly onto the retina 5. This change in optical power of the lens is called "accommodation", and is necessary in order to bring objects at different distances from the lens into sharp focus on the retina, because the distance between the lens and the retina is fixed.

As a person ages, various factors combine to reduce the ability of the eye to accommodate to objects at differing distances. Firstly, the elasticity of the lens 1 and the capsule 2 reduces with age, making it more difficult for the ciliary body 4 to compress the lens and capsule. Secondly, the ciliary body may lose strength and effectiveness, again reducing the ability of the ciliary body to change the diameter of the capsule and thus the optical power of the lens.

Intraocular lens implants have been used for many years to replace the lens in a human eye when the lens loses its transparency or becomes otherwise damaged. Early intraocular lens implants consisted of fixed-focus lenses which are inserted within the capsule to replace the natural lens, the patient being given a choice of lens either for long-distance vision or for close work, depending on the patient's preference. If the patient chose to have intraocular lenses for long-distance vision, then the patient would have to wear spectacles for close work, and vice versa.

In order to permit a degree of accommodation to a patient with an intraocular lenses, various intraocular implants have been developed in which movable optics are provided. All of these types of lenses are implanted within the capsule, and include elements referred to as "haptics" which bear on the inside surface of the capsule in alignment with the ciliary body, so that contraction of the ciliary body will compress the capsule and move the elements bearing on the inside surface of the capsule, this movement being transmitted to the lens optics to vary the optical power of the intraocular implant.

A first type of implant, described in U.S. Pat. No. 4,888, 015, provides an artificial lens of elastic material which replaces the natural lens, and is focused for short-distance vision by being radially compressed by the ciliary body, and for long-distance vision the ciliary body is relaxed and the lens returns to a flatter configuration by its own resilience.

An implant has been proposed in U.S. Pat. No. 6,767,363 to Bandhauer which comprises a pair of lens elements, joined by an annual outwardly-arching resilient framework. In this arrangement, contraction of the ciliary body acts to radially compress the arched framework, and this causes the two lens elements to be moved apart and thus the optical power of the lens combination is increased for short-distance vision. Relaxation of the ciliary body allows the two lenses to move together by a relaxation of the resilient framework, reducing the optical power of the lens combination for long-distance vision.

In a third type of implant, described in PCT publication WO 2005/084587, two optical elements are arranged within the capsule, with their optical axes slightly radially offset and with the elements bearing against diametrically opposite parts of the interior of the capsule. Contraction of the ciliary body causes the two optical elements to slide over each other in the radial direction, and the shape of the optical elements is arranged such that this radial sliding movement produces a change in the optical power of the lens combination.

In a fourth prior art arrangement, a single fixed-focus lens is suspended within the capsule by a resilient linkage which includes pads which bear against radially opposite parts of the interior of the capsule. The linkage comprises pairs of arms extending between the lens and the pads, the arms being arranged in planes which are oblique to the optical axis. Contraction of the ciliary body will compress the capsule, moving the pads closer together, and this causes movement in the arms such that the lens is maintained perpendicular to the optical axis but is moved forward (away from the retina) along the optical axis so as to bring close objects into sharp focus on the retina. Relaxation of the ciliary body allows the capsule to expand radially, the pads to move apart and the lens to move toward the retina, for accommodation to long-distance vision.

While each of the prior art arrangements disclosed above provides an intraocular lens implant with a degree of accommodation to different object distances, all of the prior art proposals rely on the ciliary muscles to radially compress the capsule in order to achieve either a change in optical power of the intraocular implant, or a change of lens position.

As a person ages, and typically in persons of 50 years of age and older, the effectiveness of the ciliary body is reduced, and the elasticity of the capsule may also be degraded such that the ciliary body is unable to effect a significant degree of movement in the capsule diameter, and thus the previous proposals for an accommodating intraocular implant will have very limited effectiveness.

There is therefore a need for an accommodating intraocular implant which does not rely on compression of the lens capsule by the ciliary body in order to effect changes in the optical power of the intraocular lens.

A principal need for an accommodating intraocular implant is to provide an ability for a person to focus on reading material such as a newspaper or book, held close to the eye. When reading, it is comfortable to hold a book or newspaper below eye level, or perhaps to support the reading material on a desk. In such situations, the reader inclines the head forward to direct the eyes downwards onto the reading material. In contrast, long-distance vision is generally required when the head is held up, so as to direct the eyes towards the horizon.

The present invention takes advantage of this movement, and seeks to provide a corrective lens arrangement having variable optical power, in which the optical power of the corrective lens arrangement varies in dependence on the orientation of the user's eye relative to the horizontal.

The corrective lens arrangement may be embodied in the form of an intraocular implant, or may be applied to extraocular device such as a pair of spectacles.

In one embodiment, the corrective lens arrangement is an intraocular lens implant comprising a lens element sensitive to the orientation of the eye, so that the optical power of the intraocular lens implant is increased when the user looks downward, and returns to a reduced optical power condition when the user's eye returns to a horizontal gaze.

Alternatively, a pair of spectacles may be provided in which the optical power of the lenses is increased when the user looks downward, and returns to a reduced optical power condition when the user lifts his head to return his eyes to a horizontal gaze.

According to a first aspect of the invention, an intraocular lens implant comprises an optical combination of a first lens element and a second lens element, securing means to fix the first lens element relative to a lens capsule with a front surface directed towards the iris of the eye, and mounting means to mount the second lens element for movement between a first position in which the optical combination has a first optical power and a second position in which the optical combination has a second, greater, optical power, the arrangement being such that movement of the eye to direct the front surface of the first lens element downwardly causes the second lens element to move to the second position, and movement of the eye to place the front surface of the first lens element in a substantially vertical plane or to direct it upwardly causes the second lens element to move to the first position.

The movement of the second lens element may be by gravity, or by the effect of buoyancy of the second lens element in the aqueous humour of the eye.

In one embodiment, the first lens element has a convex rear surface and a concave front surface, and the second lens element is pivotally mounted to the securing means and positioned in front of the first lens element, so that downward inclination of the front surface of the first lens element causes the second lens element to swing under gravity away from the first lens element. The rear surface of the first lens element may correspond in shape to the rear surface of the second lens element, so that the surfaces are in contact when the second lens element is swung towards the first lens element.

In an alternative embodiment, the second lens element is pivotally mounted behind the first lens element, so that downward inclination of the front surface of the first lens element causes the second lens element to swing under gravity towards the first lens element.

In the above embodiments, the pivot axis of the second lens element is preferably positioned above the second lens element, and above and axially spaced from the first lens element. The pivot axis may alternatively be positioned below the second lens element.

In a further alternative embodiment, the second lens element is mounted for sliding movement along a common optical axis of the first and second lens elements, and is positioned in front of the first lens element so that downward inclination of the front surface of the first lens element causes the second lens element to slide away from the first lens element.

In a yet further alternative embodiment, the second lens element is mounted for sliding movement along a common optical axis of the first and second lens elements, and is positioned behind the first lens element so that downward inclination of the front surface of the first lens element causes the second lens element to slide towards the first lens element.

It will be appreciated that the movable lens element is, in use, immersed in the liquid (aqueous humour) which fills the front part of the eye. The movable lens element may therefore be constructed to be denser than the aqueous humour, in which case the lens will tend to sink in the liquid, and may be suspended on a pivot in the manner of a pendulum. Alternatively, the movable lens element may be constructed so as to be buoyant in the aqueous humour, and may be secured to an anchor point below the movable lens element.

It is further foreseen that a buoyant second lens element may be mounted for sliding movement relative to the first, along a common optical axis. In such, arrangements, the second lens element may be mounted in front of the fixed lens, so that the buoyancy of the second lens element causes the lens elements to move together when the eye is directed downwardly. Alternatively, the second lens element may be mounted behind the fixed lens, so that the buoyancy of the second lens element causes the lens elements to move apart when the eye is directed downwardly.

In embodiments where the second, movable, lens is pivotally mounted and changes its angular orientation relative to the fixed first lens as it moves from one position to another, the movable lens may have an asymmetric "teardrop" or "pear" shape in vertical cross-section, and may be axisymmetrical so as to have a circular cross-section in horizontal planes. In such cases the second lens is preferably thinner at its region near the pivot axis. In embodiments where the second lens slides relative to the first, preserving their relative angular relationship, axisymmetric lenses, symmetrical about the optical axis, may also be used. The curvature of the surfaces of the lens elements will be arranged, in each case, so that the optical power of the lens combination is increased when the eye is directed downwardly.

A further aspect of the invention provides a package containing a first lens element for an intraocular implant of the invention, the first lens element comprising a first lens element of a predetermined optical power, fixing means for fixing the first lens element within a lens capsule, and mounting means for mounting a second lens element for movement relative to the first lens element.

A yet further aspect of the invention provides a package containing a second lens element for an intraocular implant of the invention, the second lens element comprising a lens of a predetermined optical power, and mounting means for mounting the second lens element to a first lens element for movement relative to the first lens element.

Embodiments the invention will now be described in detail with reference to the accompanying drawings, in which.

Figure 3:
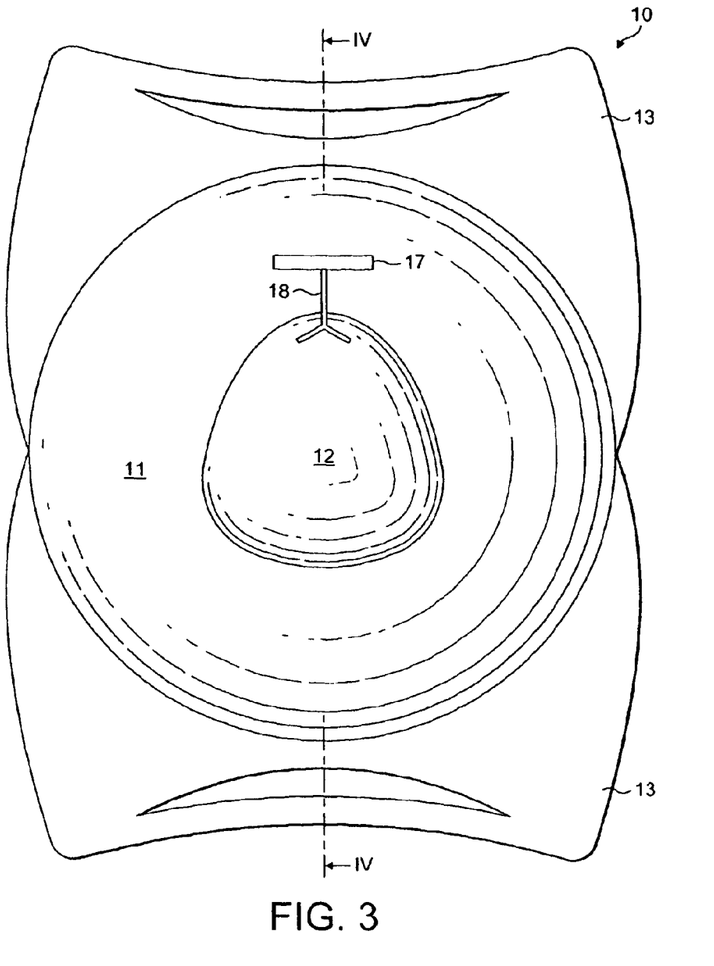
FIG. 3 is a front view of an intraocular implant according to a first embodiment the invention.
Figure 4:
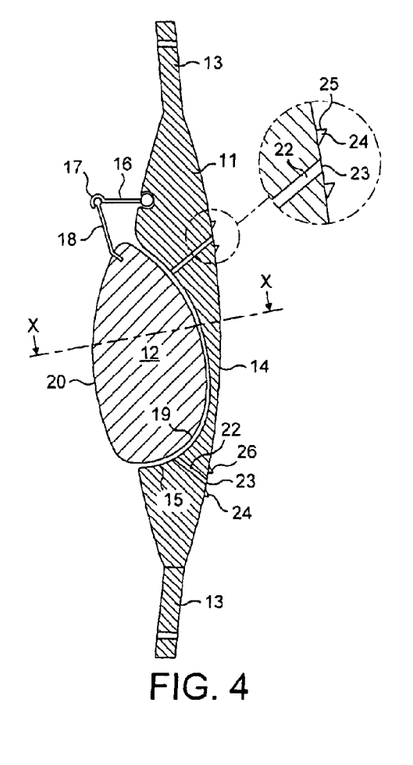
FIG. 4 is a sectional side view of the implant of FIG. 3, taken in the plane IV-IV of FIG. 3.
Figure 5:
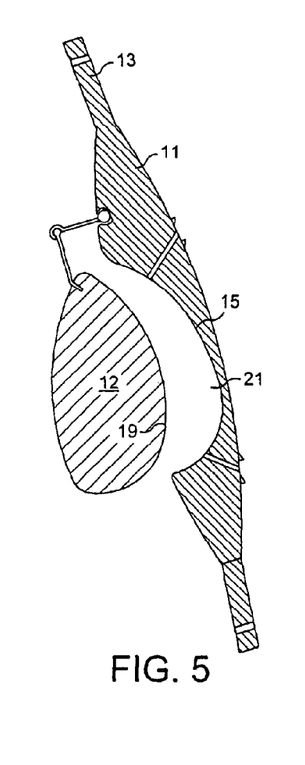
FIG. 5 is a view similar to FIG. 4, showing the movement of the second lens element as the implant is tilted.

Referring to FIGS. 3 to 5, there is shown an intraocular lens implant 10, comprising a fixed lens 11 and a movable lens 12, the movable lens 12 being pivotally mounted relative to the fixed lens 11 so that when the fixed lens 11 is inclined downwardly, such as when the user is reading, the movable lens 12 swings away from the fixed lens 11 to increase the optical power of the lens combination.

The first lens element 11 is surrounded by a fixing frame 13 dimensioned to fit within the capsule of the lens of the human eye without impeding a flow of aqueous humour within the capsule between the front and rear of the lens element 11. The first lens element 11 has a convex rear surface 14 and a concave front surface 15.

Extending forwardly from the first lens element 11 is a support 16, which at its forward end 17 is pivotally connected to a suspension rod 18. The second lens element 12 is fixed to the lower end of the suspension rod 18, so that the second lens element 12 may swing under its own weight relative to the first lens element 11 as the suspension rod 18 pivots about the forward end 17 of the support 16.

The movable second lens element 12 is shaped, in vertical section, like a teardrop or pear, with a thinner region at its upper part adjacent the suspension rod 18 and the pivot axis at the end of the support 16. The second lens element 12 has a convex rear surface 19 which substantially corresponds in form to the concave front surface 15 of the first lens element 11. The front surface 20 of the second lens element is convex. The second lens element 12 may be circular in cross-section in planes perpendicular to the major dimension of the teardrop, i.e. in planes such as plane X-X of FIG. 4.

When the user is looking at a distant object, and has his eye in a substantially horizontal gaze, the second lens element 12 hangs from the suspension rod 18 so that the first and second lens elements 11 and 12 are in close contact, with the rear surface 19 of the second lens element 12 closely adjacent to the front surface 15 of the first lens element 11. The optical power of the lens combination is arranged such that with the two lenses in this configuration, a distant object is brought to a sharp focus on the user's retina. The optical power of the lens combination will be chosen, possibly from a range of different lens combinations, with regard to the geometry of the user's eyeball.

It is foreseen that an intraocular implant system may be provided to a surgeon, the implant system comprising a fixed lens element and supporting frame, and a plurality of movable lens element assemblies each comprising a movable lens element and a pivot linkage complete with the fixed lens element. Each of the movable lens elements will have a slightly different curvature on its front surface, so that after insertion of the fixed lens element the surgeon may select a movable lens element of an appropriate optical power to attach to the fixed lens element, to provide a lens optical combination with an optical power which is appropriate to the patient's eyeball. The implant system may be produced as a single-use sterile package containing the fixed element of the implant and a plurality of movable lens elements, one of which will be selected by the surgeon and the remainder will be discarded. Preferably, however, the fixed element of the implant and the movable lens elements are packaged individually so that a surgeon can request fixed and movable elements of the appropriate optical powers for the patient concerned.

When the user inclines his gaze downward, such as to look at a close object, the head and eyeball incline forwardly to tilt the implant forward, as is shown in FIG. 5. In this configuration, the weight of the second lens element 12 causes it to swing forward under gravity about the pivot joint, separating the two lens elements such that a gap 21 opens up between the rear surface 19 of the second lens element 12 and the front surface 15 of the first lens element 11. The curvatures of the various lens surfaces are so arranged that, when the gap 21 is opened, the optical power of the lens combination is increased so that a close object is brought to a sharp focus on the user's retina.

As the user returns in his gaze to the horizontal from the downward position, the second lens element 12 will swing back, again under gravity, towards the first lens element 11, reducing the gap 21.

The positioning of the pivot point relative to the first and second lens elements may be chosen so that, when the user's gaze is generally horizontal, the second lens element 12 is held in contact with the first lens element 11, closing the gap 21 between the two lens elements 11 and 12. The curvatures of the various lens surfaces are so arranged that, when the gap 21 is closed, the optical power of the lens combination is decreased so that a distant object is brought to a sharp focus on the user's retina.

The simple pendulum linkage from which the movable lens element is suspended will cause a slight difference in the relative angular orientation of the two lens elements as the movable lens swings between its "distant" and "close" focusing positions. It is foreseen that the movable lens may be mounted on a linkage which maintains the planes of the two lens elements substantially parallel as the movable lens element moves between its "distant" and "close" focusing positions.

In order to allow aqueous humour within the gap 21 easily to escape as the lenses move together, drain passages 22 may be formed through the fixed lens element to allow liquid to escape from the gap 21 to the rear surface of the implant. It will be appreciated that, during the initial movement of the second lens element 12 away from the first lens element 11, the drain passages 22 may operate to supply liquid to the gap 21 as it opens.

In order to prevent the openings 23 of the drain passages 22 on the rear surface of the lens from becoming blocked by to tissue re-growth from the region of the "equator" of the capsule, adjacent to the edge of the intraocular implant, the rear surface of the implant may be provided with a circular ridge 24 presenting a radially outer surface 25 extending substantially perpendicularly to the rear surface of the implant. Such an abrupt transition in the surface contour of the implant is believed to impede the progress of tissue re-growth along the rear surface of the implant. A further possible mechanism to block the opening 23 of the drain passage 22 is adhesion by the capsule to the rear of the implant. In order to maintain a spacing between the interior surface of the capsule and the rear of the implant, a further ridge may be provided concentrically within the area bounded by the ridge 24. In the arrangement shown, the openings 23 of the drain passages 22 are situated in the region between the ridges 24 and 26. If contact is made between the interior of the capsule and the tops of the ridges 24 and 26, the close spacing between the ridges prevents the capsule from contacting the rear surface of the implant in the region between the ridges.

The ridges 24 and 26 may be circumferentially continuous, and drain passages (not shown) may be formed radially through the ridges to allow passage of aqueous humour in the event that the tops of the ridges 24 and 26 contact, and seal against, the interior of the capsule.

In a preferred arrangement, the ridges 24 and 26 are not circumferentially continuous but are provided with a number of short gaps. The width of each gap may be substantially equal to or less than the radial spacing between the ribs. In a particularly preferred embodiment, radially aligned gaps are provided in the two ribs 24 and 26, and the opening 23 of a drain passage is positioned centrally between the ribs at the gap position. In alternative embodiments, gaps in the outer rib 24 may be radially offset from gaps in the inner rib 26, and the openings 23 of the drain passages 22 may be positioned in the region between the ribs, optionally adjacent a gap in the inner or in the outer rib.

The support 16 may be integrally formed with the first lens element 11 and the frame 13. Alternatively, the support 16 may be a separate component or assembly, and may be fixed to the lens element 11 by a snap-engagement, or by bonding, or by some other fastening technique. Preferably, the support 16 is a substantially planar blade-like element and is received in a slot in the lens element 11, an undercut in the slot engaging with a detent on the support to retain the support 16 in the slot, once inserted. With this arrangement, a deployment technique is foreseen in which the fixed first lens element 11 is inserted into the lens capsule, and subsequently the second lens element 12, suspension arm 18 and support 16 are placed as a unit within the capsule, and the support 16 inserted into its slot. Using such a technique, the first lens element may be folded or rolled for deployment through a small opening in the capsule, and the relatively smaller second lens element may be deployed through the capsule opening subsequently.

Figure 6:
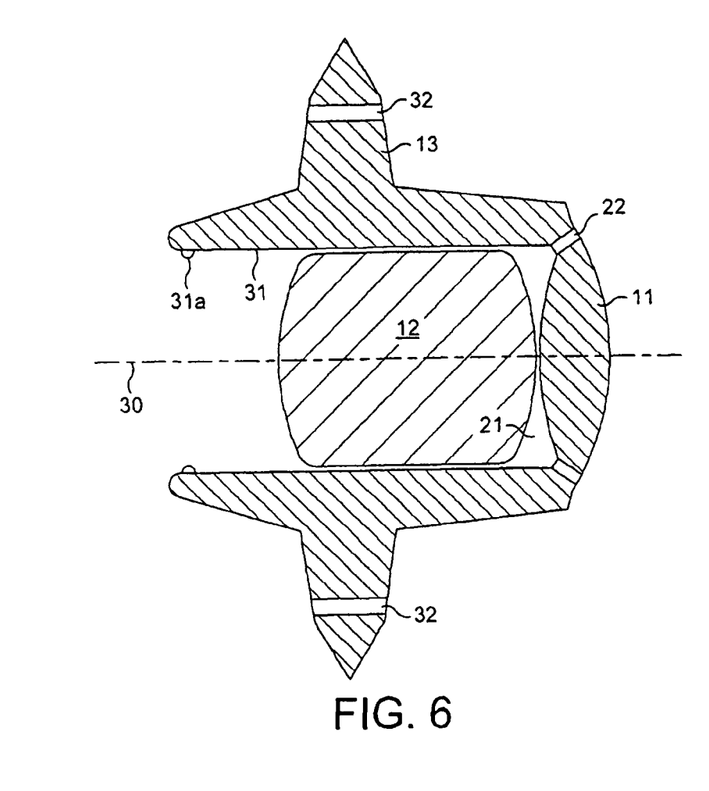
FIG. 6 is a schematic sectional view of a second embodiment of the invention.
Figure 7:
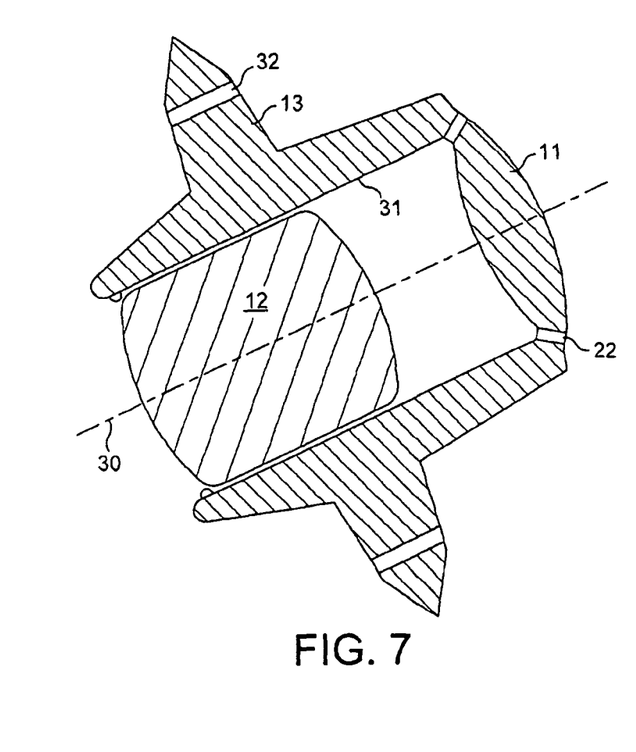
FIG. 7 is a view similar to FIG. 6, showing the movement of the second lens element as the implant is tilted.

FIGS. 6 and 7 illustrate a second embodiment of the intraocular lens implant. In this embodiment, as before, a fixed first lens element 11 is mounted to, or formed integrally with, a frame 13 which is receivable within the lens capsule of an eye. A second lens element 12 is slidingly mounted relative to the first lens element 11 so as to be movable along a common optical axis 30 towards and away from the first lens element 11. The second lens element 12 may be a cylindrical element sliding within a bore in the frame 13, or may engage the frame 13 at a plurality of separate guide surfaces extending parallel to the optical axis 30.

In the embodiment shown, the second lens element 12 slides forward within the frame 13 when the user's eye is inclined downwardly, such as when reading, to the position shown in FIG. 7. An abutment 31a may be provided to limit the movement of the lens element 12 to a predetermined maximum spacing from the fixed lens element 11. A further abutment (not shown) may be provided in front of the fixed lens element 11, to limit the rearward movement of the lens element 12, to ensure a predetermined minimum spacing from the fixed lens element 11.

When the user wishes to view objects at a distance, the user momentarily looks upward so as to allow the moving lens element 12 to slide back towards the fixed lens element 11, and thereafter the user can look at distant objects with his gaze horizontal.

A clearance may be provided between the moving lens element 12 and the bore 31, to enable aqueous humour to enter and leave the volume 21 between the fixed and moving lenses by passing round the sides of the moving lens element 12. If the moving lens element 12 is a close fit within the bore 31, drain passages 22 may be provided from the volume 21 to the rear surface of the fixed lens element 11 to enable aqueous humour to enter and leave the volume 21 between the fixed and moving lenses. Likewise, passages 32 may be provided through the frame 13 to provide fluid communication within the capsule between the front and rear surfaces of the implant.

Figure 8:
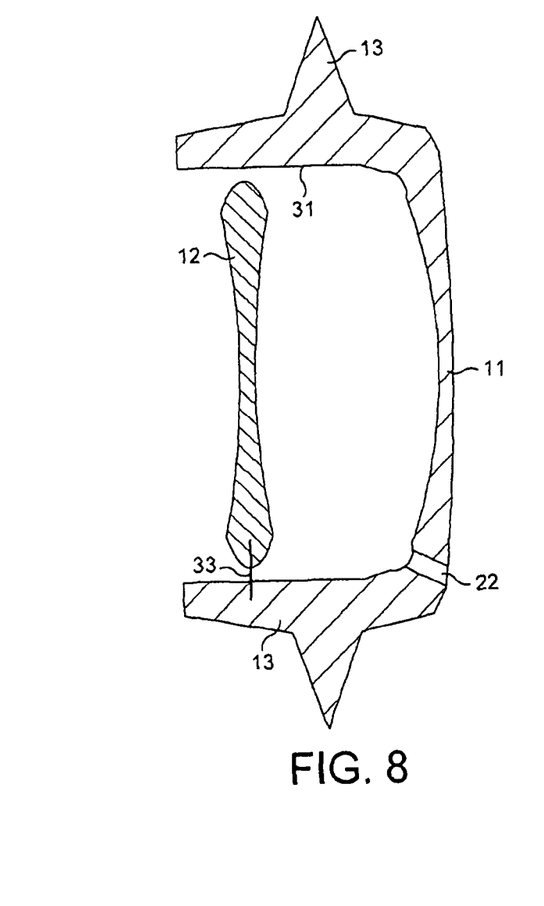
FIG. 8 is a schematic sectional view of a third embodiment of the invention.
Figure 9:
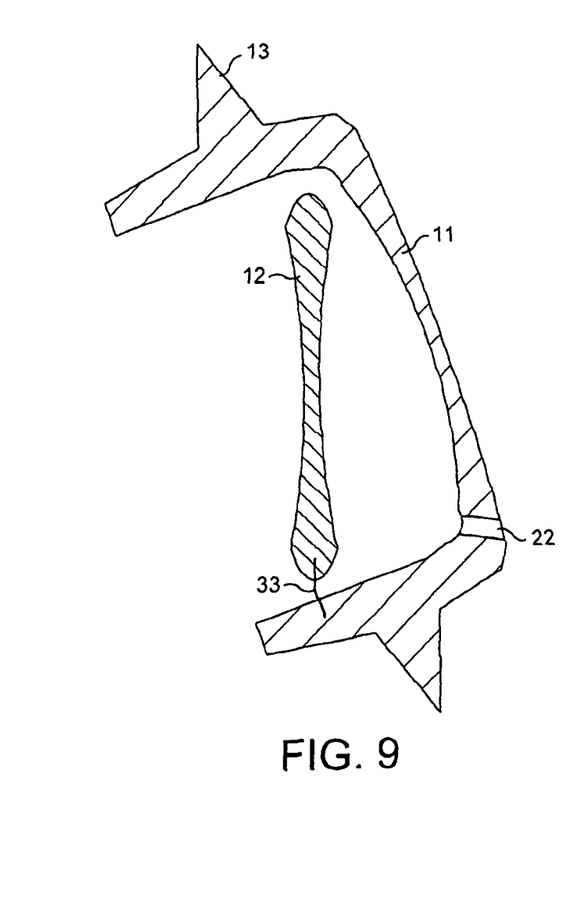
FIG. 9 is a view similar to FIG. 8, showing the movement of the second lens element as the implant is tilted.

FIGS. 8 and 9 illustrate a further embodiment of the invention, in which the intraocular implant again comprises a frame 13 for engaging the interior surface of the capsule, a fixed lens element 11, and a moving lens element 12. In this embodiment, the moving lens element 12 is movably received within a bore or cavity 31, and is anchored to a lower part of the frame 13 by a flexible joint or pivot 33. In this embodiment, be movable lens element 12 is made from a material which is less dense than the aqueous humour within which it will be immersed in use. When the eye is positioned for a horizontal gaze, such as to view a distant object, the implant is positioned as shown in FIG. 8. The buoyancy of the movable lens element 12 positions it substantially vertically above the pivot or link 33, spaced from the fixed lens element 11.

When the user inclines the eye downward, the implant occupies the position shown in FIG. 9. In this position, the frame and fixed lens are inclined downwardly, but the flexible link 33 allows the buoyant movable lens 12 to retain its substantially vertical orientation, and thus the lens 12 is moved closer to the fixed lens 11. As before, clearances or drain openings may be provided between the lens element 12 and the bore 31, or as drain passages 22 passing through the frame 13, to allow the aqueous humour to enter and leave the space 21 between the lenses 11 and 12 as the movable lens 12 changes its position.

The curvature of the surfaces of the lens elements 12 and 11 is chosen such that in the orientation of FIG. 8 a distant object is focused sharply on to the retina, enabling the user to view distant objects on the horizon, and such that in the orientation of FIG. 9 a close object is focused sharply onto the retina. The lenses in this embodiment may be biconcave, or concavo-convex lenses, as necessary.

In the embodiments described above in relation to FIGS. 6 to 9, the intraocular implant is structured such that the moving lens element is positioned to the front of the eye, with the fixed lens element between it and the retina. Alternative embodiments are foreseen in which the fixed lens element 11 is to the front of the eye, and the moving lens element 12 is between the fixed lens element and the retina. In such an embodiment, using the structure of FIGS. 6 and 7 but placing the fixed lens to the front of the eye, the moving lens element 12 will be made buoyant so that as the user inclines his eye downward the moving element 12 floats upward along the bore 31, moving away from the fixed lens element 11.

In an alternative embodiment having its fixed lens in front of the moving lens, using the structure of FIGS. 8 and 9, the moving lens element 12 will be made of material denser than the aqueous humour and the pivot or link 13 will be placed at the upper part of the movable lens 12, such that when the user inclines his eye downward the movable lens element 12 swings under gravity towards the fixed lens element 11.

The fixed lens element 11 and frame 13 may be formed from conventional materials used for intraocular implants, such as acrylic. The hinge element or elements may be formed from polymethylmethacrylate (pmma) or any other similar biocompatible material. In order to fit closely within the lens capsule, the overall diameter of the frame 13 will be preferably from 10 to 11 mm, with the diameter of the moving lens being from 5 to 6 mm in the embodiment shown in FIGS. 3 and 4.

The invention claimed is:

1. An intraocular lens implant comprising:
an optical combination of a first lens element and a second lens element;
securing means to fix the first lens element relative to a lens capsule with a front surface directed towards the iris of the eye; and
mounting means to mount the second lens element for pivoting movement under gravity between a first position in which the second lens is adjacent the front surface of the first lens and the optical combination has a first optical power, and a second position in which the second lens is spaced from the first lens and the optical combination has a second optical power greater than the first optical power;
wherein the second lens element has an asymmetric "teardrop" or "pear" shape with a thinner region at its upper part, and the arrangement being such that directing the front surface of the first lens element downwardly causes the second lens element to move to the second position, and directing the front surface of the first lens element horizontally or upwardly causes the second lens element to move to the first position.

2. An intraocular implant according to claim 1, wherein the second lens element is pivotally suspended adjacent the front surface of the first lens element.

3. An intraocular implant according to claim 1, wherein the front surface of the second lens element is convex.

4. An intraocular implant according to claim 1, wherein the second lens element is circular in cross-section in planes perpendicular to a major dimension of the teardrop.

5. An intraocular implant according to claim 1, wherein the front surface of the first lens element comprises a concave surface portion, and the adjacent surface of the second lens element is convex and substantially corresponds in form to the concave surface portion of the first lens element.

6. An intraocular implant according to claim 1, wherein the surfaces of the first and second lens elements are configured such that the optical power of the optical combination is increased as the lenses are moved apart.

7. An intraocular implant according to claim 1, wherein the rear surface of the fixed lens is formed with a ridge substantially surrounding the central region of the rear surface.

8. An intraocular implant according to claim 7, wherein the ridge is an annular ridge presenting a radially outer surface substantially perpendicular to the surface of the fixed lens.

9. An intraocular implant according to claim 7, wherein the ridge includes one or more circumferential discontinuities or gaps.

10. An intraocular implant according to claim 7, further comprising a drain passage penetrating through the fixed part of the implant from the front surface of the first lens element to the rear surface of the first lens element, and opening on the rear surface of the first lens element at a point within the area bounded by the annular ridge.

11. An intraocular implant according to claim 10, wherein the ridge includes one or more circumferential discontinuities or gaps, and the opening of the drain passage is aligned with a gap in the ridge.

12. An intraocular implant according to claim 7, further comprising a second ridge formed concentrically with the first.

13. An intraocular implant according to claim 12, wherein the second ridge has one or more gaps.

14. An intraocular implant according to claim 13, wherein the first ridge includes one or more circumferential discontinuities or gaps, and a gap in the second ridge is radially aligned with a gap in the first ridge.

15. An intraocular implant according to claim 12, further comprising a drain passage penetrating through the fixed part of the implant and opening on the rear surface of the implant at a point within the area between the two ridges.

16. An intraocular implant according to claim 15, wherein the drain passage opens on the rear surface of the implant in an area radially aligned with a gap in the first or second ridge.

* * * * *